(12) United States Patent
Sakumura et al.

(10) Patent No.: US 9,945,961 B2
(45) Date of Patent: Apr. 17, 2018

(54) RADIATION DETECTOR, AND X-RAY ANALYSIS APPARATUS AND RADIATION DETECTION METHOD USING THE SAME

(71) Applicant: Rigaku Corporation, Akishima-shi, Tokyo (JP)

(72) Inventors: Takuto Sakumura, Hachioji (JP); Yasukazu Nakaye, Ome (JP); Masataka Maeyama, Hamura (JP); Kazuyuki Matsushita, Ome (JP)

(73) Assignee: RIGAKU CORPORATION, Tokyo (JP)

( * ) Notice: Subject to any disclaimer, the term of this patent is extended or adjusted under 35 U.S.C. 154(b) by 0 days.

(21) Appl. No.: 15/680,833

(22) Filed: Aug. 18, 2017

(65) Prior Publication Data

US 2017/0371044 A1 Dec. 28, 2017

Related U.S. Application Data

(63) Continuation of application No. 14/522,717, filed on Oct. 24, 2014.

(30) Foreign Application Priority Data

Nov. 15, 2013 (JP) .................................. 2013-237225

(51) Int. Cl.
*G01T 1/00* (2006.01)
*G01N 23/00* (2006.01)
(Continued)

(52) U.S. Cl.
CPC ............... *G01T 1/18* (2013.01); *G01N 23/04* (2013.01); *G01N 23/207* (2013.01); *G01T 1/026* (2013.01);
(Continued)

(58) Field of Classification Search
CPC .................................... G01T 1/24; G01T 1/16
See application file for complete search history.

(56) References Cited

U.S. PATENT DOCUMENTS 5,296,816 A 3/1994 Birkinshaw

FOREIGN PATENT DOCUMENTS

| DE | 100 12 337 A1 | 10/2001 |
|---|---|---|
| JP | 64-57189 A | 3/1989 |

(Continued)

OTHER PUBLICATIONS

Hasegawa et al., "Development of a shutterless continuous rotation method using an X-ray CMOS detector for protein crystallography", Journal of Applied Crystallography, vol. 42, 2009, pp. 1165-1175.

(Continued)

*Primary Examiner* — Dani Fox
(74) *Attorney, Agent, or Firm* — Birch, Stewart, Kolasch & Birch, LLP (57) ABSTRACT

There are provided a radiation detector capable of detecting radiation without occurrence of dead time while maintaining an exposure state in which radiation enters continuously, and an X-ray analysis apparatus and a radiation detection method using the radiation detector. A radiation detector 100 that detects radiation in synchronization with an external apparatus 200, includes: a sensor 110 that generates pulses when radiation particles are detected; a plurality of counters 140a, 140b provided so as to be able to count the pulses; and a control circuit 160 configured to switch a counter to count the pulses among the plurality of counters 140a, 140b, when receiving a synchronization signal from the external apparatus 200.

7 Claims, 7 Drawing Sheets

(51) Int. Cl.
    *G01T 1/18*     (2006.01)
    *G01T 1/17*     (2006.01)
    *G01T 1/24*     (2006.01)
    *G01N 23/207*     (2018.01)
    *G01T 1/02*     (2006.01)
    *G01N 23/04*     (2018.01)

(52) U.S. Cl.
    CPC ............ *G01T 1/171* (2013.01); *G01T 1/24* (2013.01); *G01N 2223/643* (2013.01)

(56) References Cited

FOREIGN PATENT DOCUMENTS

| | | |
|---|---|---|
| JP | 10-126692 A | 5/1998 |
| JP | 2830482 B2 | 12/1998 |
| JP | 2003-75373 A | 3/2003 |
| WO | WO 91/00612 A1 | 1/1991 |

OTHER PUBLICATIONS

Hulsen et al., "Protein crystallography with a novel large-area pixel detector", Journal of Applied Crystallography, vol. 39, 2006, pp. 550-557.

Office Action issued in Japanese Application No. 2013-237225 dated Nov. 1, 2016 w/ an English translation.

|  | Ave.counts | MEASURED REFLECTION NUMBER | INDEPENDENT REFLECTION NUMBER | Rmerge | R($>2\sigma$) |
|---|---|---|---|---|---|
| WORKING EXAMPLE 1 | 2627 | 8631 | 1455 | 1.50% | 2.63% |
| COMPARATIVE EXAMPLE 1 | 2781 | 8709 | 1451 | 1.57% | 2.67% |

FIG. 7

RADIATION DETECTOR, AND X-RAY ANALYSIS APPARATUS AND RADIATION DETECTION METHOD USING THE SAME

CROSS-REFERENCE TO RELATED APPLICATIONS

This application is a Continuation of copending application Ser. No. 14/522,717, filed on Oct. 24, 2014, which claims priority under 35 U.S.C. § 119(a) to Application No. 2013-237225, filed in Japan on Nov. 15, 2013, all of which are hereby expressly incorporated by reference into the present application.

BACKGROUND OF THE INVENTION

Field of the Invention

The present invention relates to a radiation detector that detects radiation in synchronization with an external apparatus, and to an X-ray analysis apparatus and a radiation detection method using the same.

Description of the Related Art

Conventionally, a CCD detector has been used as a radiation detector. A certain time is necessary for the CCD detector to read out data, and thus, if exposure is performed at the time of data readout, variation may occur in exposure time depending on the position of a detection screen. Reflecting such a situation, exposure has been performed in a procedure where a shutter is opened after preparation of CCD exposure is completed and data is read out after the shutter is closed. For example, in FIG. 4 in Patent Document 1, shutter timing is described for a single crystal X-ray structure analyzing method.

As mentioned above, since a shutter is opened and closed during detection in the CCD detector, shutterless measurement is impossible. In measurement for a single crystal structure analysis, if several hundreds to several thousands of images are shot while rotating the crystal in one process of measurement, a shutter is opened and closed for every shooting, resulting in a big loss in time.

In addition, as for a general semiconductor detector with no buffer function, readout time is present. In the readout time, data exposure is not performed, and thus, even if shutterless measurement will be performed, data missing time will occur.

Contrary to such a traditional technology presupposing shutter open/close operation, a method for detecting an X ray using a CMOS detector with the shutter being kept open has been proposed. In Non-patent Document 1, a new high-speed, high-accuracy method for measuring diffraction data using an X-ray CMOS detector is proposed. In the method described in Non-patent Document 1, diffraction images are read out in a constant time period while a crystal is rotated continuously with the shutter being kept open. In addition, although a continuous sample rotation mode is also described in Non-patent Document 1, as illustrated in FIG. 3, a dead time is present as readouts.

On the other hand, technologies utilizing readout of a plurality of lines from a detector have been disclosed. In Patent Document 2, a method for reading data onto two storage areas out of a two-dimensional image detection section by dividing the data into odd lines and even lines is described. In addition, Patent Document 3 describes a plurality of times of readout operations of each light receiving element during continuous exposure of the two-dimensional image detection section.

Patent Document 1: JP-A-2003-75373
Patent Document 2: JP-A-H10-126692
Patent Document 3: Japanese Patent No. 2830482
Non-patent Document 1: Kazuya Hasegawa, Kunio Hirata, Tetsuya Shimizu, Nobutaka Shimizu, Takaaki Hikima, Seiki Baba, Takashi Kumasaka and Masaki Yamamoto, "Development of a shutterless continuous rotation method using an X-ray CMOS detector for protein crystallography", Journal of Applied Crystallography, 2009, 42, 1165-1175
Non-patent Document 2: Gregor Hulsen, Christian Broennimann, Eric F. Eikenberry and Armin Wagner, "Protein crystallography with a novel large-area pixel detector", Journal of Applied Crystallography, 2006, 39, 550-557

As mentioned above, there is a method for reading out the diffraction image of a sample at a fixed time interval with the shutter being kept open, but, even in such a method, the dead time occurs at the detector side, and thus, continuous exposure of a detector has not been realized yet. In addition, although there is a technology for utilizing readouts of a plurality of lines from a detector, continuous exposure using the technology has not been realized yet.

SUMMARY OF THE INVENTION

The present invention is made in view of such a situation, and has an object to provide a radiation detector capable of detecting radiation without occurrence of dead time while maintaining an exposure state where radiation enters continuously, and X-ray analysis apparatus and radiation detection method using the same.

DETAILED DESCRIPTION OF THE INVENTION (1) Aiming at achieving the above-mentioned object, the radiation detector of the present invention is a radiation detector that detects radiation in synchronization with an operation of an external apparatus, and includes: a sensor that generates pulses when radiation particles are detected; a plurality of counters provided so as to be able to count the pulses; and a control circuit configured to perform continuous exposure while switching a counter to count the pulses among the plurality of counters at a timing of receiving a trigger signal from the external apparatus.

With this configuration, radiation can be detected without occurrence of dead time while maintaining the exposure state where radiation enters continuously. As a result, measuring time is shortened and measurement can be accelerated. In addition, statistical errors can be reduced, thus, enabling a high accuracy measurement.

(2) In addition, the radiation detector of the present invention further includes a readout circuit configured to perform reading from the counter that has finished counting immediately before between timings of receiving a trigger signal from the external apparatus. With this configuration, counts can be read out from one counter during operation of another counter and switching to the next counter can be prepared, thus, enabling continuous exposure.

(3) In addition, the radiation detector of the present invention includes two counters as the plurality of counters. With this configuration, exposure can be maintained without dead time by a simple circuit configuration.

(4) In addition, the radiation detector of the present invention includes three or more counters as the plurality of counters. With this configuration, exposure can be continued without occurrence of dead time even if the exposure time is shorter than the readout time.

(5) In addition, the radiation detector of the present invention receives a signal for specifying time or a position as the trigger signal from the external apparatus. With this configuration, counters can be switched depending on, for example, the operation timing of an external apparatus, the position of an arm, or the position of an analysis target.

(6) In addition, the X-ray analysis apparatus of the present invention includes a mechanism configured to cause an X-ray to enter continuously; and the radiation detector that detects the X-ray caused to enter. With this configuration, an X-ray measurement by continuous exposure is enabled, and for example, if it is an X-ray diffraction measurement, high accuracy measurement with small Rmerge is enabled.

(7) In addition, the radiation detection method of the present invention is a radiation detection method for detecting radiation in synchronization with an operation of an external apparatus, including the steps of: counting pulses generated when radiation particles are detected with one of a plurality of provided counters; switching a counter to count the pulses among the plurality of counters provided so as to be able to count the pulses at a timing of receiving a trigger signal from the external apparatus; and reading count data from the counter which has finished counting immediately before, at the same time of switching the counter, wherein a series of steps is repeated until measurement is finished. With this method, radiation can be detected without occurrence of dead time while maintaining the exposure state where radiation enters continuously.

According to the present invention, radiation can be detected without occurrence of dead time while maintaining the exposure state in which radiation enters continuously.

BEST MODES FOR CARRYING OUT THE INVENTION

Embodiments of the present invention will now be described with reference to drawings. In order to facilitate understanding of explanation, in each drawing, to the same component, the same reference number is attached and the duplicated explanation will be omitted.

First Embodiment (Configuration of a Detector)

Figure 1:
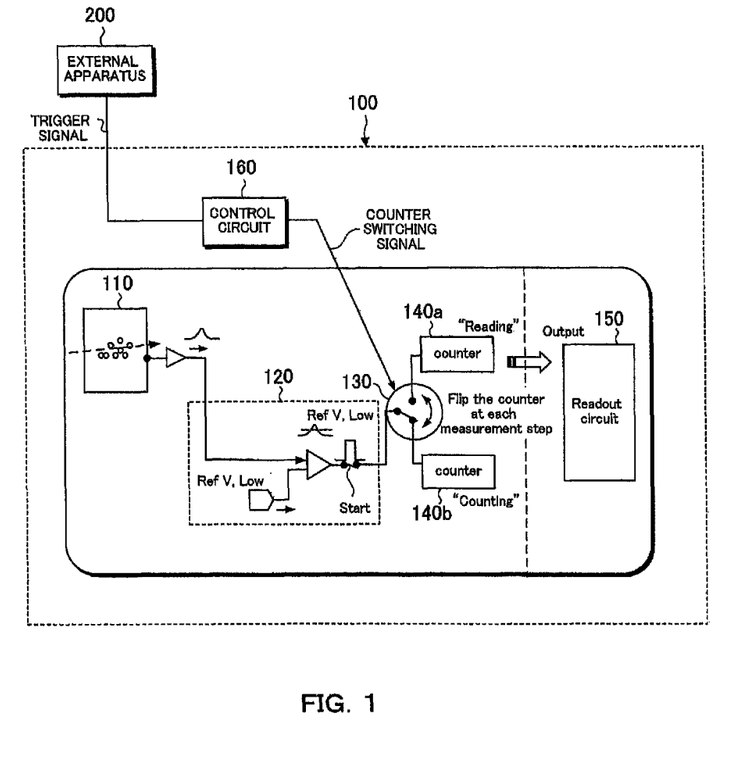
FIG. 1 is a schematic view illustrating the configuration of a radiation detector.

FIG. 1 is a schematic view illustrating the configuration of a radiation detector 100. The radiation detector 100 is a semiconductor detector for detecting radiation in synchronization with an external apparatus, and has a two-dimensional data buffer function. The radiation to be detected is likely to exhibit a function when it is an X-ray, but may not be limited to this but may be α-ray, β-ray, γ-ray, neutron-ray, etc. In addition, the radiation detector 100 may be a one-dimensional detector.

As illustrated in FIG. 1, the radiation detector 100 includes a sensor 110, a detection circuit 120, a switching circuit 130, a first counter 140a and a second counter 140b, a readout circuit 150, and a control circuit 160. The sensor 110 generates pulses when radiation particles are detected. The sensor 110 can detect the strength of the X-ray flux which enters a light-receiving surface as surface information.

The detection circuit 120 determines whether or not a pulse is higher than a reference value, and when the pulse is higher, sends it out to a counter under counting among the plurality of counters 140a and 140b as a voltage signal. The switch circuit 130 switches the counter to count the voltage signal, when having received a counter switching signal of the control circuit 160.

Each of the two counters 140a and 140b has an equivalent function, and can count pulses. In the example illustrated in FIG. 1, two counters are provided, but, three or more counters may be provided (described later). When using two counters, exposure can be maintained without dead time by a simple circuit configuration.

The readout circuit 150 reads out a count value from the counter which has finished counting immediately before. It is preferable to read the count value at the same timing of the counter switching. By finishing reading the count value from the counter promptly, the counter can be returned into a countable state at an early stage.

The control circuit 160 switches a counter to count pulses among a plurality of counters, when having received a synchronization signal from the external apparatus 200. With this operation, radiation can be detected without occurrence of dead time while maintaining the exposure state where the radiation enters continuously. As a result, measuring time is shortened and measurement can be accelerated. In addition, a situation, in which a statistical error becomes larger than that of original measurement due to dropping of counts due to the readout time, can be solved, and the statistical error can be reduced, thus, enabling high accuracy measurement.

As a synchronization signal from the external apparatus 200, for example, a signal for specifying time or a position can be received. This allows counter switching depending on, for example, the operation timing of the external apparatus, the position of an arm, or the position of an analysis target.

The readout circuit 150 reads out count data from the counter 140a, which has finished counting immediately before, between timings of receiving a trigger signal from the external apparatus 200. This makes it possible to read out count data from one counter 140a during operation of another counter 140b, and to allow the counter 140a to prepare start of counting by next switching, thus, enabling continuous exposure.

(Operation of a Detector)

Figure 2:
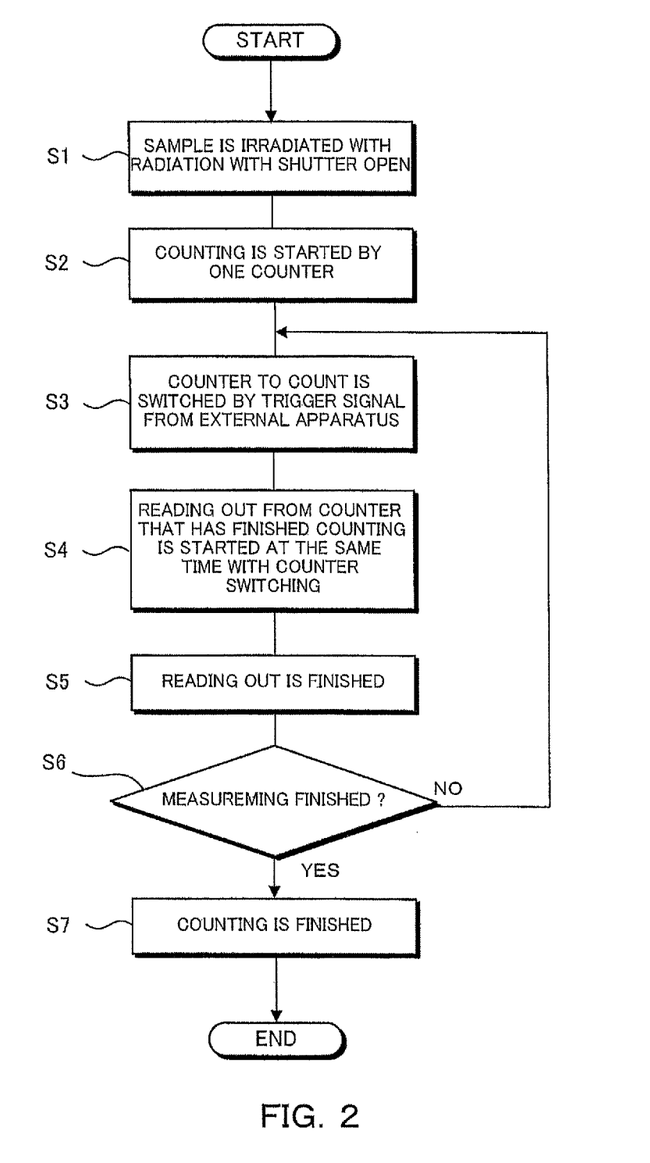
FIG. 2 is a flowchart illustrating the operation of the radiation detector.

The operation of the radiation detector 100 configured as above will now be described. FIG. 2 is a flowchart illustrating the operation of the radiation detector 100.

A sample is first irradiated with radiation with a shutter being kept open (step S1). When radiation particles having entered a detection plane are detected by a sensor 110, pulses are generated. Initially, one counter starts measuring radiation (step S2). Pulses are counted by another counter.

Upon reception of a trigger signal from the external apparatus 200, the control circuit 160 switches a counter to count pulses among the plurality of counters 140a, 140b (step S3). This makes it possible to detect radiation without occurrence of dead time while maintaining the exposure state where radiation enters continuously.

At the same time, the readout circuit 150 starts to read out count data from a counter which has finished counting (step S4). A counter to count continues counting, and reading out count data from a counter which has finished counting prior to the timing of counter switching is completed (step S5).

After that, whether the measurement is finished or not is determined (step S6). When the measurement is not finished, the process returns to step S3, and the counters are switched after receiving a trigger signal from the external apparatus. In this way, step S3 to step S6 will be repeated until the measurement is finished. On the other hand, when it is determined that the measurement is finished in step 6, counting will be finished and the measurement will be finished.

Figure 3:
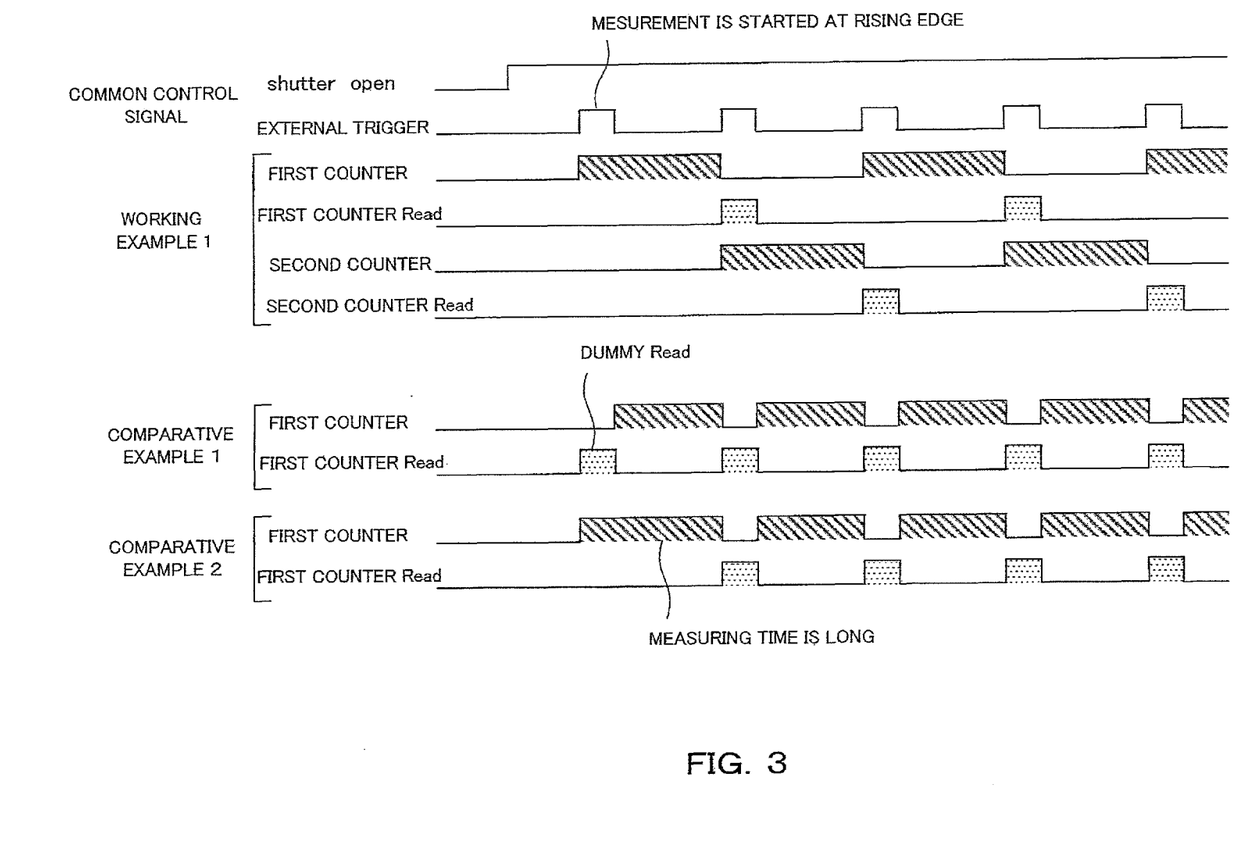
FIG. 3 is a timing-chart illustrating a working example and a comparative example.

Such an operation will now be described using a timing chart in comparison with a conventional operation. FIG. 3 is a timing chart illustrating a Working Example and a Comparative Example. Common control signals illustrated in FIG. 3 indicate a shutter open/close signal and a trigger signal from the external apparatus, respectively. As illustrated in the drawing, the shutter is maintained to be always in an open state. In addition, as the trigger signal from the external apparatus 200, for example, a direction signal for moving the arm of a goniometer or a signal generated every given time interval can be used.

In Working Example 1, radiation is detected in continuous exposure without dead time by using two counters and switching them alternately. In Working Example 1, a first counter starts counting at the rising edge of a trigger signal. A second counter is initially in a wait state and after the counters are switched at the rising edge of a next trigger signal starts counting. Further, reading out of the first counter which has finished counting is started at the same time of the switching. Subsequently, by utilizing the rising edge of the trigger signal, the counters can be switched alternately, and count data can be read out.

In comparative examples 1 and 2, radiation is detected using one counter. In comparative example 1, reading out is started at the edge of a trigger signal from the external apparatus 200. Initially, dummy reading out operation is performed and then reading out of the count data of the first counter is started when counting of the first counter is finished at the edge of the trigger signal. This makes it unnecessary to discard initial count data. The second counter starts counting at the timing when reading out is finished. In this way, counting by the first counter and reading out of the count data are repeated.

In Comparative Example 2, the first counter starts counting at the edge of the trigger signal from the external apparatus 200. Initial count time becomes longer than the subsequently repeated count time. In Comparative Example 2, it is necessary to discard the initial count data. Then, reading out of the count data is started when the first counter has finished counting at the edge of the trigger signal. Counting is started at the timing when the reading out has finished. In this way, counting by the first counter and reading out of the count data are repeated.

In Working Example 1, the count time of the first and second counters is continuing without dead time. In both cases of Comparative Examples 1 and 2, the dead time due to readout time has occurred, and continuous exposure is not enabled.

Second Embodiment

Figure 4:
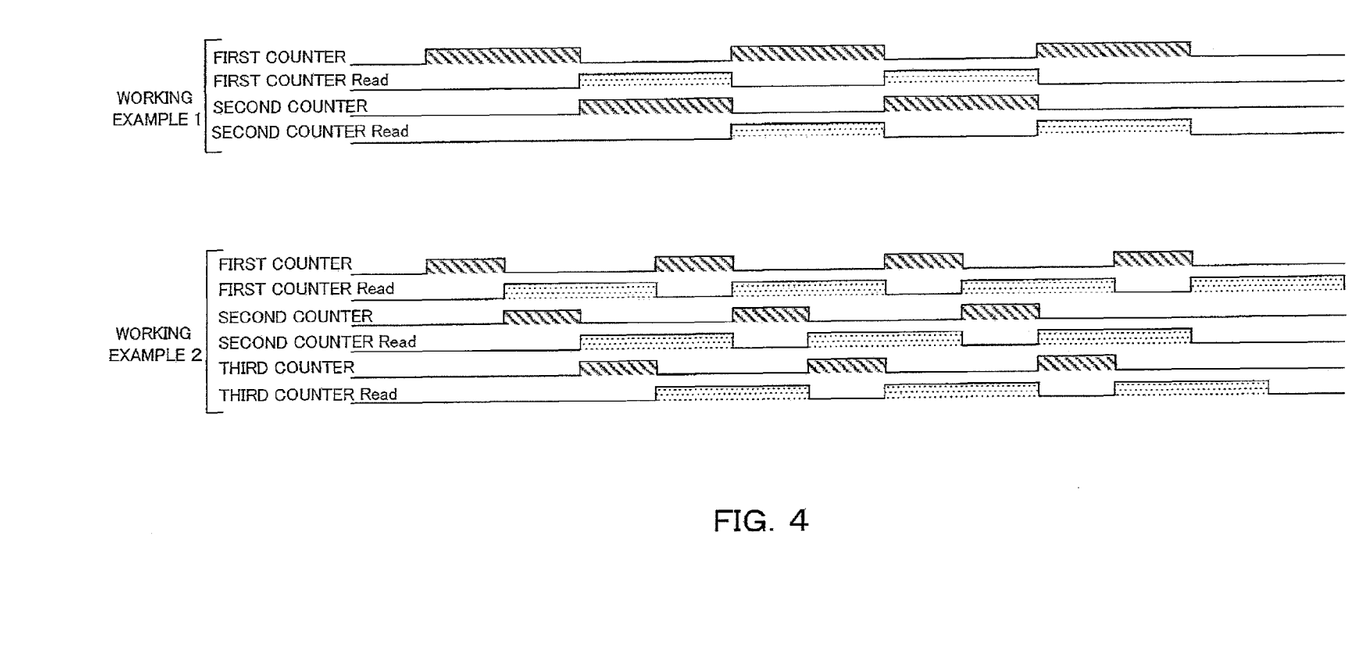
FIG. 4 is a timing-chart illustrating a case of using two counters and a case of using three counters.

In the above-mentioned embodiment, two counters are provided and a counter to count is switched between them, but, it is also possible to switch the counter to count in sequence among three or more counters. This enables exposure to continue without occurrence of dead time even in a case where exposure time is shorter than readout time. FIG. 4 is a timing chart illustrating a case where two counters (first and second counters) are used (Working Example 1), and a case where three counters (first to third counters) are used (Working Example 2).

In Working Example 1 illustrated in FIG. 4, count time (exposure time) of each counter is set to be shortest in a case where two counters are provided, and count time coincides with the readout time from each counter. That is, in the case where two counters are used, in order to prevent dead time from occurring, it is necessary to satisfy the condition: exposure time ≥readout time.

On the contrary, in Working Example 2 illustrated in FIG. 4, count time (exposure time) of each counter is set to be shortest in a case where three counters are provided, and count time coincides with a half of the readout time from each counter. That is, in the case where three counters are used, in order to prevent dead time from occurring, it is necessary to satisfy the condition: exposure time ≥(readout time)/2. In this way, even in a case of three or more counters, if a suitable data buffer or parallel readout means, etc. is provided, it is possible to eliminate dead time with exposure time equal to or lower than readout time. However, in a case using a buffer, total exposure time is limited by the size of the buffer.

Third Embodiment (Single Crystal Analysis Apparatus)

Figure 5:
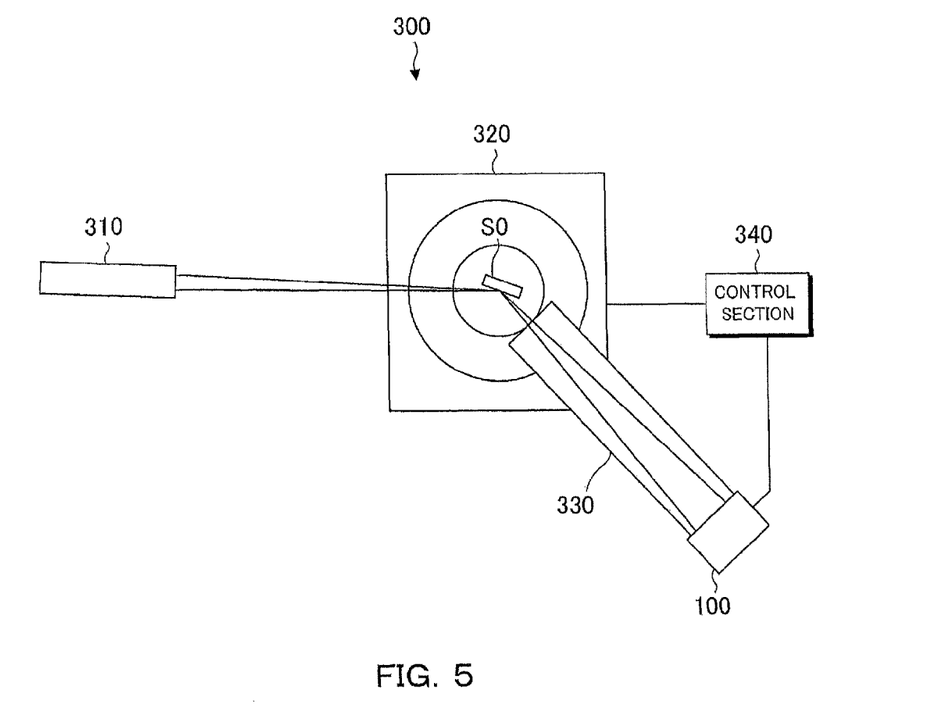
FIG. 5 is a plan view illustrating an example of an X-ray analysis apparatus.

The radiation detector as mentioned above can be assembled in an X-ray analysis apparatus. FIG. 5 is a plan view illustrating an example of an X-ray analysis apparatus 300. The X-ray analysis apparatus 300, which is a single crystal structure analysis apparatus, includes an X-ray source 310; a sample table 320; an arm 330; a control unit 340; and an X-ray detector 100. The X-ray source 310 is shutterless, and radiates X-rays on a sample S0 continuously.

Measurement can be performed without stopping the measurement axis of a goniometer with the shutter open without repeating opening/closing the shutter during measurement, thus, enabling to improve the throughput of measuring time. The detector can control the amount to measure by a signal from the goniometer while being in the exposure state to output measured data for each synchronization of the goniometer signal.

The sample table 320 and the arm 330 are interlocked with each other, and can be rotated around the sample S0 at a constant speed by control of the control section 340. The radiation detector 100 is provided to the end of the arm 330 and the movement around the sample S0 is controlled together with the arm 330.

The X-ray analysis apparatus 300, which includes the radiation detector 100 as mentioned above, can count X-rays under continuous exposure without dead time by switching a counter using, for example, a control signal for moving the arm from the control section 340 as a trigger signal. This enables to obtain an X-ray diffraction image in continuous angles.

As a result, for example, in case of X-ray diffraction measurement, high accuracy measurement with small Rmerge is enabled. In addition, by performing continuous measurement (TDI, etc.) using a synchronization signal, measurement without considering data missing corresponding to readout time is also enabled.

Fourth Embodiment (Production Line)

Figure 6:
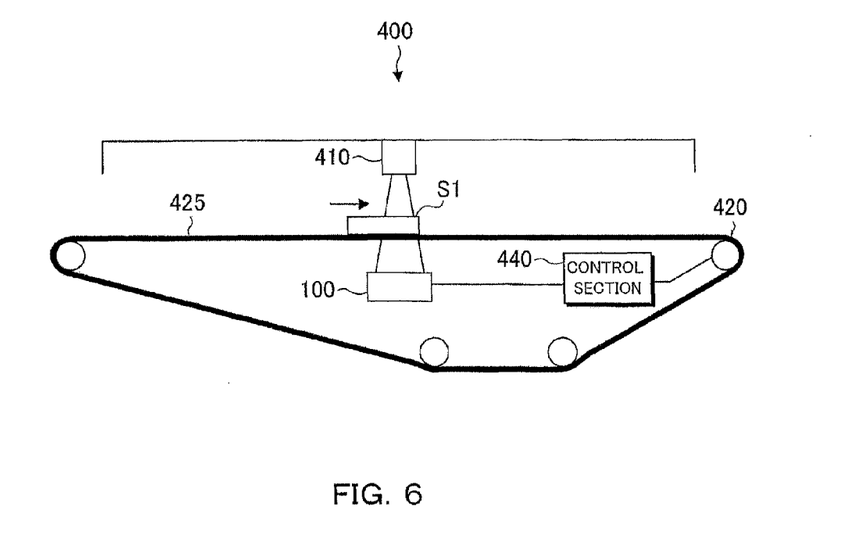
FIG. 6 is a side view illustrating an example of the X-ray analysis apparatus.

FIG. 6 is a side view illustrating an example of an X-ray analysis apparatus 400. The X-ray analysis apparatus 400 is a production line where X-ray inspection is possible, and includes an X-ray source 410; a roller 420; a belt 425, a control section 440; and a radiation detector 100. The X-ray source 410 is shutterless, and radiates X-rays on a product S1 continuously.

The belt 425 is moved by rotation of the roller 420 to transfer the product S1 in an arrow direction of the drawing, The belt 425 is moved at a constant speed by control of the control section 440. The radiation detector 100 is provided to the side opposite to the X-ray source 410 across the belt 425 and the product S1, and the transfer of the belt 425 and the product S1 are controlled.

Since including the radiation detector 100 as mentioned above, the X-ray analysis apparatus 400 can count X-rays under continuous exposure without dead time by switching counters using, for example, a belt control signal from the control section 440 as a trigger signal.

Experiment

The present inventor carried out experiments using the configuration of the above X-ray analysis apparatus 300 under controls of Working Example 1 and Comparative Example 1 illustrated in FIG. 3. In Comparative Example 1, only the first counter was used. The camera length was 45 mm, and the moving angle per one frame was 0.5 degree. Further, exposure condition was 2 sec/frame.

Figure 7:
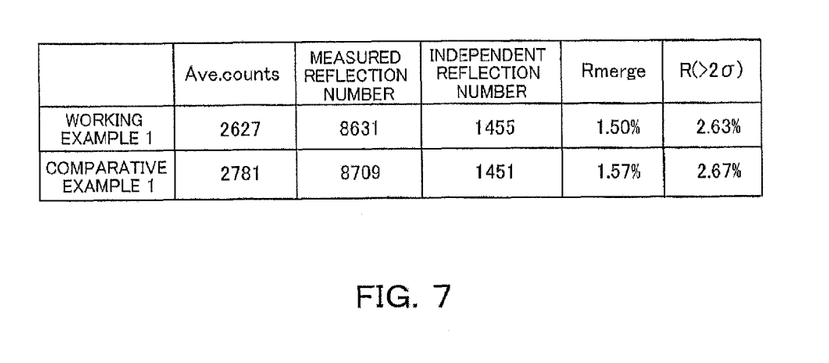
FIG. 7 is a table indicating experimental results.

FIG. 7 is a table indicating experimental results. As shown in FIG. 7, in Working Example 1, an X-ray diffraction image (the average count value: 2627, measured reflection number: 8631, independent reflection number: 1455) was able to be shot, and an experimental result with Rmerge of 1.50% and R($>2\sigma$) of 2.63% was obtained. Further, in Comparative Example 1, an X-ray diffraction image (the average count value: 2781, measured reflection number: 8709, independent reflection number: 1451) was able to be shot, and an experimental result with Rmerge of 1.57% and R($>2\sigma$) of 2.67% was obtained. Both of the results of Rmerge and R($>2\sigma$) in Working Example 1 were more preferable than those in Comparative Example 1.

The invention claimed is:

1. A radiation detector that detects radiation in synchronization with an operation of an external apparatus, the radiation detector supported by an arm and including:
    a sensor that generates pulses when radiation particles from an analysis target subject to a radiation detection placed on a sample table are detected;
    a plurality of counters provided so as to be able to count the pulses; and
    a control circuit configured to perform continuous exposure while switching a counter to count the pulses among the plurality of counters at a timing of receiving a trigger signal from the external apparatus,
    wherein the trigger signal is a control signal for movement of at least one of the arm and the analysis target.

2. The radiation detector according to claim 1, further comprising:
    a readout circuit configured to perform reading from the counter that has finished counting immediately before between timings of receiving a trigger signal from the external apparatus.

3. The radiation detector according to claim 1, further comprising:
    two counters as the plurality of counters.

4. The radiation detector according to claim 1, further comprising:
    three or more counters as the plurality of counters.

5. The radiation detector according to claim 1, wherein the radiation detector receives a signal for specifying time or a position as the trigger signal from the external apparatus.

6. An X-ray analysis apparatus, comprising:
    a mechanism configured to cause an X-ray to enter continuously; and
    the radiation detector according to claim 1 that detects the X-ray caused to enter.

7. A radiation detection method for detecting radiation by a radiation detector supported by an arm in synchronization with an operation of an external apparatus, comprising the steps of:
    counting pulses generated when radiation particles from an analysis target subject to a radiation detection placed on a sample table are detected with one of a plurality of provided counters;
    switching a counter to count the pulses among the plurality of counters provided so as to be able to count the pulses at a timing of receiving a trigger signal from the external apparatus; and
    reading count data from the counter which has finished counting immediately before, at the same time of switching the counter, wherein
    a series of steps is repeated until measurement is finished, and
    the trigger signal is a control signal of movement of at least one of the arm and the analysis target.

* * * * *